United States Patent [19]

Daste

[11] Patent Number: 5,019,398

[45] Date of Patent: May 28, 1991

[54] PHARMACEUTICAL COMPOSITION PROVIDING THE SUSTAINED-RELEASE OF VALPROIC ACID

[75] Inventor: Georges Daste, Eysines, France

[73] Assignee: Sanofi, Paris, France

[21] Appl. No.: 483,721

[22] Filed: Feb. 23, 1990

[30] Foreign Application Priority Data

Feb. 27, 1989 [FR] France ................................. 8902493

[51] Int. Cl.$^5$ ............................................... A61K 9/36
[52] U.S. Cl. ..................................... 424/480; 424/475; 424/482; 424/488; 514/557
[58] Field of Search ................. 424/480, 475; 514/557

[56] References Cited

U.S. PATENT DOCUMENTS 4,301,176  11/1981  Grabowski ........................... 424/318
4,558,070  12/1985  Baller .................................... 514/557

FOREIGN PATENT DOCUMENTS 8430755  7/1984  Australia .
1136351  11/1982  Canada .............................. 260/438.1
0133110  2/1985  European Pat. Off. .

OTHER PUBLICATIONS

Chemical Abstracts, vol. 105, No. 24, Dec. 15, 1986, p. 321.
Chemical Abstracts, vol. 110, No. 20, May 15, 1989, p. 404.

*Primary Examiner*—Thurman Page
*Assistant Examiner*—D. Gabrielle Phelan
*Attorney, Agent, or Firm*—Wegner, Cantor, Mueller & Player

[57] ABSTRACT

The object of the invention is a tablet sustaining release for more than 8 hours, the active ingredient of which is constituted by the complex formed between one mole of valproic acid and one mole of sodium valproate.

5 Claims, No Drawings

PHARMACEUTICAL COMPOSITION PROVIDING THE SUSTAINED-RELEASE OF VALPROIC ACID

The present invention relates to a sustained-release anti-epileptic pharmaceutical composition based on valproic acid.

Valproic acid and several of its derivatives: salts, amides and esters, have long been used in human therapy for the treatment of epilepsy. The value of a sustained-release form to patients who have to make long-term use of this drug is obvious; it enables the number of daily administrations to be reduced. However, in the case of this drug, it offers other advantages which include the suppression of blood level peaks, which is important since it has been observed that the difference between the effective dose and the toxic dose is slight in some patients, but also because the risks of intolerance and side effects are reduced for all patients and because it is sufficient to take a single blood sample to determine the metabolic response of each patient to the drug, whereas with the standard pharmaceutical forms the considerable variations in the absortion and elimination of the drug from one individual to another make it necessary to verify the blood level attained for a given dose.

Meir Bialer et al., in Biopharmaceutics & drug disposition 5, p. 1–10 (1984), have reported the results of a pharmacokinetic study in the dog of a sustained-release form of valproic acid; however, the patent application in which their composition should have been described was never published and it seems that the studies were not pursued.

At the same time, in EP-A-0 133 110, a sustained-release pharmaceutical composition based on valproic acid and sodium valproate was described; this composition, constituted of a water-insoluble matrix of acrylic polymer (Eudragit$^R$) and ethylcellulose, weighs 680 mg for 333 mg of sodium valproate and 145 mg of valproic acid, which corresponds to a quite voluminous tablet which some patients find difficult to swallow.

A sustained-release pharmaceutical composition has now been found, having the form of a tablet of moderate weight and volume while containing 500 mg of active ingredient which is slowly released throughout the entire duration of gastrointestinal transit, i.e. 8 to 10 hours. The active ingredient is constituted by the complex salt described in the patent EP-34172, formed between one molecule of valproic acid and one molecule of valproate sodium; the weight of the excipients in the sustained-release tablet according to the invention is at the most 1/5 of the weight of the active complex. Furthermore, and this could not have been foreseen, the correlation between the dose administered and the blood concentration of the drug is excellent, whereas with standard forms there was—usually—no proportional relationship between the dose and the blood level. Finally, in subjects suffering from severe epilepsy, who are treated by the simultaneous administration of several drugs, it has been noted that it is possible to reduce the doses of the associated drugs.

This tablet is constituted of a hydrophilic and gelifiable matrix of hydroxypropylmethylcellulose of very high viscosity, from 8000 mPa.s to 12000 mPa.s, and preferably about 10000 mPa.s. Under such conditions, for 100 mg of the mole-for-mole complex of acid and salt, 8 to 10 mg of hydroxypropylmethylcellulose suffice to form a sufficiently thick an viscous network to give in vivo a gel which effectively slows down the release of active ingredient.

In order to make possible the compression of such a mixture of complex and hydroxypropylmethylcellulose, whether directly or after granulation, and in particular in order to prevent sticking, a minimal quantity of a both lubricating and absorbing excipient, such as hydrated silica known under the trade name Levilite, is added; in fact, it has been observed that the standard lubricants such as talc or magnesium stearate do not prevent sticking on compression whereas 8 to 10 mg of hydrated silica, preferably mixed with 1 to 2 mg of collodial silica, per 100 mg of complex suffice to form a compressible mixture giving a non-friable tablet.

From 1 to 4 mg of a fluidizing agent such as collodial silica and a synthetic sweetening agent such as aspartame or saccharin may optionally be added; the latter is advantageous in the case of divisible tablets to mask the bitterness of the active ingredient. Other products usually used in the technology may be included but it is important to note that the above formula can be compressed without the addition of a diluting excipient such as cellulose or lactose, which would increase the volume of the tablet.

Before carrying out the compression in a standard apparatus, the mixture of the excipients and the active ingredient is preferably granulated with an organic solvent, such as alcohol, a ketone or a halogenated solvent and preferably with ethanol, by a known technique; it has been observed that the time taken for the release of the active ingredient depends very little on the degree of compression once it exceeds the minimal value necessary to form a coherent tablet, and this ensures excellent reproductibility of the batches manufactured without imposing undue technical constraints.

The tablet is advantageously coated with a varnish which facilitates swallowing and masks the unpleasant taste of the active ingredient; this varnish does not need to be gastroresistant since it has been noted that, although there is only about 10% by weight of retarding agent relative to the weight of the active ingredient supposed to be soluble in the gastric medium, its release into the stomach is less than 5%, and this avoids the phenomena of gastric intolerance well-known with this type of compound.

The film-forming agents soluble in organic solvents usually used are polyacrylates, polymethacrylates of low molecular weight, esters or salts of the type marketed by Rohm Pharma under the trade name Eudragit, for example, catalogue numbers NE 30D or E 100. It has been observed that these varnishes adhere poorly to the tablet according to the invention and a fine intermediate layer of hydroxypropylmethylcellulose with very low viscosity, for example 5 to 20 mPa.s, is deposited before the final layer. This first layer of varnish is deposited in an organic solvent selected from those which are usually used for such an operation, such as alcohols, ketones and methylene chloride. Aqueous solvents which would hydrate the hydroxypropylmethylcellulose network of the tablet are avoided. The external layer can then be deposited in an aqueous solvent such as an aqueous alcoholic solvent or water.

The tablets according to the invention advantageously contain the equivalent of 500 mg of valproic acid which makes possible the administration of only one tablet per day for the treatment of patients who usually receive 2 to 3 times a day the pharmaceutical compositions with an enteric coating presently on the market and which contain 125, 250 or 500 mg of valproic acid.

In the following, a tablet according to the invention, a process for its preparation and the results of a comparative pharmacokinetic study are described.

EXAMPLE 538.2 g of the solid complex formed by mixing one molecule of valproic acid and one molecule of sodium valproate is mixed with 46.8 g of hydroxypropylmethylcellulose of viscosity 10,000 mPa.s and the mixture obtained is moistened with 50 g of ethanol before granulation is performed in a high energy granulator mixer. After being dried, the granulate is calibrated on a grid of 1 to 1.6 mm mesh size, then mixed with 49.2 g of Levilite$^R$ of about 5μm diameter, 2.9 g of colloidal silica and 2.9 g of saccharin sodium.

The mixture is compressed by a force of 1500 to 2500 deca-newtons with a 17×9 mm punching rod with a dividing blade. Each 640 mg tablet contains 538.2 mg of complex which corresponds to 500 mg of valproic acid. The uncoated tablets are varnished by spraying in a coating turbine supplied with hot air.

For the first layer, a solution consisting of 94.8 g of methylene chloride, 42 g of ethyl alcohol, 2.8 g of glycerol and 7.2 g of hydroxypropylmethylcellulose of viscosity 15 mPs.s is sprayed on to 640 g of the previously prepared tablets.

For the second layer, suspension consisting of 78 g of ethyl alcohol, 5 g of water, 0.3 g of titanium dioxide, 0.44 g of talc, 1.6 g of polyethylene glycol 1500, 2.1 g of hydroxypropylmethylcellulose of viscosity 15 mPa.s, 4.765 g of cationic polymethacrylate (Eudragit E 100) and 0.795 g of a neutral copolymer of methacrylic and acrylic acids (Eudragit NE 30 D in aqueous suspension, i.e. 2.65 g of suspension) is sprayed.

One tablet according to the invention and one capsule containing 538.2 g of the complex formed between valproic acid and its sodium salt were administered successively, at an interval of more than 4 days, to two healthy subjects. The blood concentration of the active ingredient (valproic acid or its salt) was determined by the usual technique; the results obtained are shown in Table I

TABLE I

|  | TABLET | | CAPSULE | |
|---|---|---|---|---|
|  | subject A | subject B | subject A | subject B |
| max. blood concentration (μg/ml) | 27,6 | 27,5 | 61,6 | 56,7 |
| time to attain the maximum (hour) | 10 | 12 | 0,5 | 1,3 |
| area under the curve (μg · h/ml) | 772,4 | 834,8 | 780,2 | 928,7 |

I claim:

1. A tablet sustaining release for more than 8 hours, the active ingredient of which is constituted by the complex formed between one mole of valproic acid and one mole of sodium valproate, and excipients comprising 8% to 10% by weight relative to the weight of the complex of a matrix of hydroxypropylmethylcellulose of viscosity from 8000 to 12000 mPa.s, and 8% to 10% by weight relative to the weight of the complex of hydrated silica.

2. The tablet of claim 1, comprising in addition from 1 to 2% by weight of colloidal silica relative to the weight of the complex.

3. A tablet according to claim 1, which is coated with a varnish composed of 2 layers, the first of which is essentially formed of hydroxypropylmethylcellulose of viscosity between 5 and 20 mPa.s and the external layer is based on film-forming polyacrylates or polymethacrylates.

4. A tablet according to claim 2, which is coated with a varnish composed of 2 layers, the first of which is essentially formed of hydroxypropylmethylcellulose of viscosity between 5 and 20 mPa.s and the external layer is based on film-forming polyacrylates or polymethacrylates.

5. A unit dose tablet comprising 538 mg of valproic acid and sodium valproate complex, 45 mg to 50 mg of a matrix of hydroxypropylmethylcellulose of viscosity about 10000 mPa.s, 45 to 50 mg of hydrated silica and 3 mg of colloidal silica.

* * * * *